United States Patent
Glimelius et al.

(10) Patent No.: US 10,315,047 B2
(45) Date of Patent: Jun. 11, 2019

(54) METHOD, COMPUTER PROGRAM AND SYSTEM FOR OPTIMIZING RADIOTHERAPY TREATMENT

(71) Applicant: RaySearch Laboratories AB, Stockholm (SE)

(72) Inventors: Lars Glimelius, Stockholm (SE); Tore Ersmark, Farsta (SE); Martin Janson, Enskededalen (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 15/533,420

(22) PCT Filed: Jun. 23, 2016

(86) PCT No.: PCT/EP2016/064551
§ 371 (c)(1),
(2) Date: Jun. 6, 2017

(87) PCT Pub. No.: WO2016/207286
PCT Pub. Date: Dec. 29, 2016

(65) Prior Publication Data
US 2017/0333733 A1    Nov. 23, 2017

(30) Foreign Application Priority Data
Jun. 26, 2015    (EP) .................... 15173971

(51) Int. Cl.
*A61N 5/10* (2006.01)
(52) U.S. Cl.
CPC .... *A61N 5/1031* (2013.01); *A61N 2005/1087* (2013.01); *A61N 2005/1095* (2013.01); *A61N 2005/1096* (2013.01)

(58) Field of Classification Search
CPC .... A61N 2005/1087; A61N 2005/1095; A61N 5/1031; A61N 5/103
See application file for complete search history.

(56) References Cited

U.S. PATENT DOCUMENTS

| | | | | |
|---|---|---|---|---|
| 2004/0165696 A1* | 8/2004 | Lee | ...... | A61N 5/1031 378/65 |
| 2006/0045238 A1* | 3/2006 | Nguyen | ...... | A61N 5/103 378/65 |
| 2010/0046706 A1* | 2/2010 | Moreau | ...... | A61N 5/103 378/65 |

FOREIGN PATENT DOCUMENTS

| | | |
|---|---|---|
| JP | H11-299906 A | 11/1999 |
| WO | WO-2007/012185 A1 | 2/2007 |
| WO | WO-2008/114159 A1 | 9/2008 |

OTHER PUBLICATIONS

Krämer et al., "Treatment planning for heavy-ion radiotherapy: physical beam model and dose optimization," Physics in Medicine and Biology, vol. 45, pp. 3299-3317 (2000).

(Continued)

*Primary Examiner* — Wyatt A Stoffa
(74) *Attorney, Agent, or Firm* — Drinker Biddle & Reath LLP

(57) ABSTRACT

An optimization method for ion based radiotherapy includes inverse planning based on optimization variables related to the particle energy, a range modulator or ridge filter, a block and/or a range compensator. This enables automatic optimization of complex cases.

13 Claims, 2 Drawing Sheets

(56) References Cited

OTHER PUBLICATIONS

Li et al., "A novel patch-field design using an optimized grid filter for passively scattered proton beams", Phys. Med. Biol., (2007), vol. 52, pp. N265-N275.

* cited by examiner

METHOD, COMPUTER PROGRAM AND SYSTEM FOR OPTIMIZING RADIOTHERAPY TREATMENT

This application is the National Stage of International Application No. PCT/EP2016/064551, filed June 23, 2016, and claims benefit of European Patent Application No. 15173971.1 filed June 25, 2015.

TECHNICAL FIELD

The present invention relates to radiation therapy planning, and in particular to optimization of ion therapy in which a tumour is targeted with a beam of ions (e.g. protons or heavier ions like carbon).

BACKGROUND AND RELATED ART

Radiotherapy is commonly used for treating diseases such as cancer. Various types of radiation sources may be used. The predominant type of radiation used today is photon radiation. Although more expensive than photon radiotherapy, ion based therapy methods, such as proton and carbon therapy, are becoming more common because of their advantages. While photons will pass through a patient's body and emit energy along the whole path, ion beams are subject to very little lateral scattering and can be made to stop at a desired depth in the patient's body. Also, an ion beam will emit an increasing amount of energy as it travels within the body, until it stops. It is possible to plan the treatment in such a way that the ions are made to stop immediately after they pass the desired target area, typically a tumour. Hence, ion radiotherapy may be planned to emit most of its energy in the desired target area and less to surrounding tissue, as compared to photons.

Two main techniques are used for ion radiotherapy: passive therapy and pencil beam scanning. In passive therapy a broad field of radiation is applied and physical elements are used to shape the beam to match the target as precisely as possible. The beam energy will control the maximum range of the beam in the patient. The width of the high dose region, i.e. the Spread Out Bragg Peak (SOBP), is controlled by for example a range modulator or ridge filter. The basic principle is that multiple energies are combined with different weights so that the high dose region is flat, either accomplished by the different steps in a range modulator or by the shape of the ridges in a ridge filter. The other physical elements typically include a block of a non-permeable material such as tungsten or brass, forming a tunnel having the desired shape through which the beam is passed in order to shape it laterally. Another element is the range compensator, which is placed in the beam trajectory to affect the maximum depth of the beam in the patient's body. The compensator shortens the local range of the ion beam and is non-uniformly shaped to compensate for the shape of the tumour. The depth of the target is given as water equivalent depth and depends on the geometrical distance as well as the density and material distribution along the beam path. In areas where the beam should travel a shorter water equivalent depth within the patient, the range compensator will be thicker than in other areas. In pencil-beam scanning a large number of small (pencil) beams are used to cover the tumour in all three dimensions. This is achieved by changing the intensity, position and range of each beam individually. Note that a block and range compensator can be used with the pencil beam scanning technique as well. The main purposes are to sharpen the lateral beam edge (penumbra), and to make each energy layer fit the tumor better, respectively.

One of the main challenges therefore is to design the block and the compensator to shape and modulate the ion beam, so that it will travel the exact distance to the remote end of the tumour along a given beam passing through the tumour. This is traditionally achieved by ray tracing of the patient geometry, which means computing the intersection of the tumour area with the beam coming from the radiation source, taking into account the material composition along the way, and using this information to shape the block and compensator.

WO2008/114159 discloses an apparatus and a method primarily for photon based radiotherapy treatment planning. A treatment planner is used to optimize the treatment based on a weighted combination of treatment objectives, such as dose objectives, treatment device objectives such as the energy provided by the treatment device, and treatment device parameter objectives, such as attenuator or MLC settings, or objectives related to the time rate of change.

Solutions developed for photon based radiotherapy cannot be easily applied to ion based radiotherapy. In particular, the devices used to modulate and shape the beam are different. It should be noted that although devices called compensators are used both for photon based radiotherapy and for ion based radiotherapy these compensators are of fundamentally different nature. The compensator used for photons attenuates the photon beam by removing photons from the beams. The compensator used for ions adjusts the range of the ions, that is, the water equivalent distance they will travel inside the patient's body. This latter type of compensator may therefore be referred to as a range compensator.

For complex patient geometries and tumour shapes, the computation may become very difficult. Some cases may be so complex that it may be practically impossible to create an optimal plan manually. For example, where a critical organ is blocking a portion of the target from the radiation source, a technique called patching may be used, in which different portions of the target are radiated by ion beams from different angles to entirely avoid the critical organ. In such cases, it is difficult to achieve a uniform dose distribution at the border areas between the ion beams. Li et al.: A novel patch-field design using an optimized grid filter for passively scattered proton beams, Phys. Med. Biol. 52 (2007) N265-N275 discloses a patching strategy in which a part of a target is subjected to a through field and another part of the target is subjected to a patch field that is supposed to form a uniform, roughly L-shaped field together with the through field. To compensate for the imperfections in the border area between the patch field and the through field Li et al. propose manipulating the compensator to design the distal fall off of the patch field by means of a grid filter using a repetitive pattern of different material thicknesses of the compensator. This creates a blurring effect at the distant fall-off region, making it possible to match the gradient in the lateral fall off of the main beam. While this may improve the dose uniformity in the border area it will only target this particular case. It will for example not handle cases where the uniformity is different in different parts of the patch region. Furthermore it is not a general method to design the beam energy, range modulator, block and compensator for any beam design.

SUMMARY OF THE INVENTION

It is therefore an object of the invention to enable improved optimization of radiotherapy treatment plans using ion therapy.

The invention relates to a method of optimizing a radiotherapy plan for ion therapy where an ion beam is shaped by means of passive devices including at least one of the following: energy adapting means for adapting the beam energy for changing the maximum range of the beam, a block and a range compensator, the method comprising the following steps:
a. defining an objective function comprising at least one dose objective related to a dose to be delivered to a region of a patient,
b. defining an initial value set comprising at least one initial value for at least one optimization variable related to the at least one of the passive devices and defining the initial value set as current value set,
c. determining a dose distribution resulting from the current value set,
d. evaluating the dose distribution with respect to the dose objectives,
e. determining if the objective function should be evaluated for another value set and if so, performing step f, otherwise jumping to step g,
f. modifying at least one initial value in the initial value set to create a modified value set, and defining the modified value set as the current value set before returning to step c,
g. selecting one of the value sets to use in the radiotherapy.

In accordance with the invention inverse planning is used to determine the final shape of the passive devices.

This enables automatic optimization of the passive devices, reducing the amount of manual editing needed to create the treatment plan. Thus, according to the invention, the quality of a treatment plan could be improved compared to prior art methods, especially for complex cases, and high quality treatment plans can be determined also for cases that are too complex to handle manually. Also, a treatment plan can be created in less time than with the prior art methods.

As discussed above, the means for adapting the SOBP width may be either a range modulator or a ridge filter. The block is provided to shape the beam laterally. The beam energy is adapted to affect the maximum depth of the beam in the patient's body. The range compensator is arranged mainly to affect the local range of the ion beam and is non-uniformly shaped to compensate for the shape of the tumour.

Another advantage is the possibility to take uncertainties (e.g. in beam range and patient setup) into account. Since the method according to the invention is based on optimization algorithms, rather than forward planning, it is possible to use robust optimization. This makes it possible to take into account uncertainties for example in the patient's exact position or the beam range The determining in step e) is preferably based on whether or not the dose distribution satisfies the dose objectives within a certain tolerance. In a preferred embodiment a maximum deviation from the dose objective is set and in step e) it is determined to continue with step g) when a dose distribution that differs from the dose objective by less than the maximum deviation is reached by a modified value set. This ensures that the resulting treatment plan will fulfil minimum quality requirements.

Alternatively, in step e) it is determined to continue with step g) when a specified number of value sets have been evaluated, wherein the value set that provides the best match with the dose objective is selected. The two different criteria for step e) may also be combined, for example so that the procedure will continue with step g) if a satisfactory dose distribution is achieved, but if, after calculating the specified number of value sets, the maximum deviation has still not been fulfilled, the process continues with step g).

As is common in the art, the dose objective preferably includes a minimum dose for a selected region of the patient and/or a maximum dose for a second selected region of the patient.

In a preferred embodiment the passive devices include a block having a block aperture for shaping the beam, and the initial value set includes the size and/or shape of the block aperture. As is common in the art, the block aperture may be defined in terms of pixels or in terms of vertices in the block contour polygon.

In a preferred embodiment the initial value set includes a first and a second thickness value in at least a first and a second portion of the range compensator, respectively and/or a value related to the SOBP range and width resulting from the beam energy and the choice of range modulator.

In a particularly preferred embodiment the initial value set comprises at least one initial value for each of at least two optimization variables related to at least two of the passive devices. This enables the treatment plan to be optimized based on two or more optimization variables at once. Preferably, in this case the initial value set includes a first and a second thickness value in at least a first and a second portion of the range compensator and at least one other optimization parameter.

The invention also relates to a computer program product comprising computer readable code means which, when run in a computer will cause the computer to perform the inventive method according to any of the embodiments above. The computer program product is typically stored on a carrier such as a hard disk, a memory stick or any other type of memory suitable for holding a computer program.

The invention also relates to a computer system for performing dose calculations for radiotherapy, the system comprising processing means and having a program memory having stored therein a computer program product as defined above, in such a way that the computer program product, when executed, will control the processing means.

Preferably, the computer system further comprises a data memory arranged to hold data to be used by the processing means when performing the optimization method, such as image data related to the patient, an initial treatment plan and/or information related to at least one scenario.

BRIEF DESCRIPTION OF THE DRAWINGS

The invention will be described in more detail in the following, with reference to the appended drawings, in which.

DETAILED DESCRIPTION OF PREFERRED EMBODIMENTS

Figure 1:
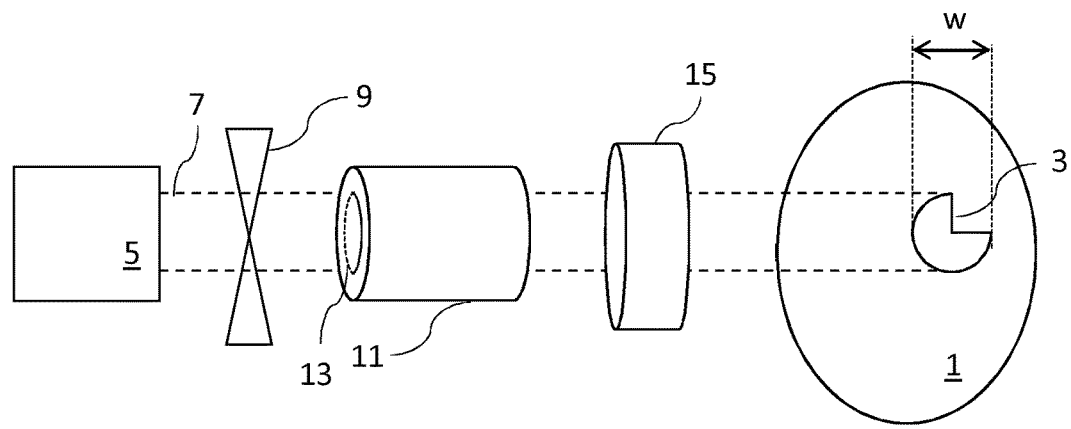
FIG. 1 shows an example of a system for passive ion therapy

FIG. 1 shows schematically an example of a system for passive ion therapy in which the invention may be implemented. A patient 1 that is to be subjected to ion therapy is shown schematically to the right in FIG. 1. A region of interest ROI, or target 3, within the patient 1 represents the organ or other tissue that is to receive the radiotherapy. The maximum width of the target 3 is marked as w. As is common in the art, there may also be defined critical areas within the patient, which are areas in which it is particularly important to avoid radiation, although this is not shown in FIG. 1.

A radiation source 5 provides an ion beam 7 having a sufficient energy to achieve the desired maximum range, typically reaching to the distal target 3 edge. Typically one or two scattering devices (not shown) is arranged to create a broad field of radiation. Alternatively a uniform scanning technique or wobbling may be used to create a broad field. In pencil beam scanning technique, where the intensity is non-uniform over the beam, scattering devices are not needed. Still a block and/or a compensator may be used to make an energy layer conform to the shape of the target. The dose is subsequently shaped to the target, that is, the region of interest, using passive devices. First, in the path of the radiation, a range modulator 9 is arranged, in order to create the spread out Bragg peak as will be discussed in more detail in connection with FIG. 4. In short, the range modulator 9 determines the width w (along the beam direction) of the SOBP, which should be wide enough to cover the area of the target 3. After the range modulator 9 a block 11 is arranged to shape the beam laterally. The block 11, typically made from brass or some other material that will not be penetrated by the ions, has an aperture 13 for letting the beam through. The target 3 typically has an irregular shape so that the water equivalent distance to the distal edge of the target will vary over the target. For example, in FIG. 1, the lower portion of the target 3 extends further into the patient's body 1 than the upper portion. The patient geometry will also affect the (water equivalent) distance to the target. For calculating the distance the beam has to travel inside the body, the body tissues are assumed to have the same properties as water, whereas bone or air pockets will affect the distance in different ways. A bone region in the beam path will for example increase the water equivalent depth, while an air cavity will reduce it, as compared to the geometrical distance.

The beam energy is chosen so that the maximum ion beam range agrees with the most distal point on the target. Of course, more complex patient geometries and target shapes often occur, and the range will be too large for at least some of the target. To compensate for the variation in water equivalent distance to the distal end of the tumour, a range compensator 15 is introduced to control the local range over the cross-section of the ion beam. Although this is not shown in FIG. 1, the thickness of the range compensator varies across the beam trajectory in a way well known in the art to adapt the beam energy to the distal end of the target in each point. By adding a corresponding amount of compensator material in front of the patient at a certain position, the range will be shortened and the dose will conform to the target distal edge. This should be controlled as precisely as possible, to avoid unnecessary radiation to parts of the patient outside of the ROI. The range compensator 15 is arranged to shorten the range of the ion beam to a different degree in different points of the range compensator, so that in any point of the ROI the ion beam will reach as far as the distal end of the ROI.

A block 11 and a range compensator 15 may also be used during a pencil beam scanning treatment. In this case the ion beam is created by means of a large number of small pencil beams with different positions, ranges and intensities. This scanning technique gives the possibility to conform the dose well to the target. Therefore, the block is mainly used for sharpening the penumbra, that is, the lateral edges of the beam. The range compensator 15 may be used in this case to ensure that the highest energy layer coincides with the distal edge of the target 3. Hence, the underlying principles of the present invention are not restricted to passive therapy systems and methods but may be used in all types of ion therapy systems.

Figure 2:
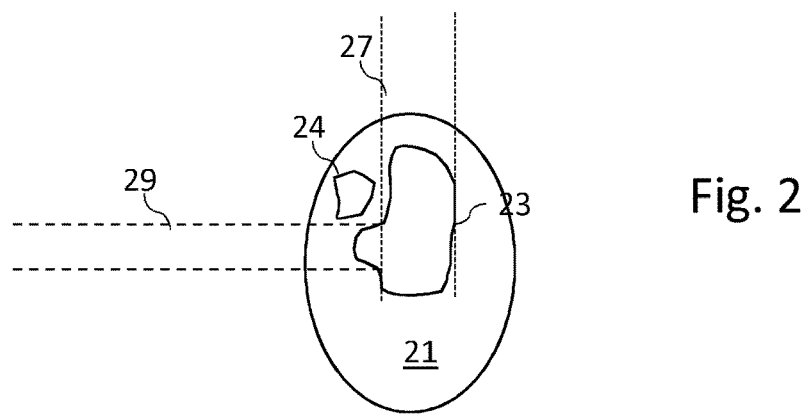
FIG. 2 illustrates a setup for ion therapy in which two radiation fields are patched together using a method according to the invention.

The aim of the radiation therapy is to provide a uniform yet conformal dose to the target 3 and as little radiation as possible outside of the target. This may be difficult because of beam spread. Heterogeneous patient geometries and complex target shapes will add to the difficulties. In some particularly complex situations two or more radiation fields are patched and/or matched together to provide a uniform dose to the entire target. Such an example can be seen in FIG. 2, which shows, schematically, a patient 21 comprising a target ROI 23 where part of the target 23 is blocked by a critical organ 24, which is to receive no radiation. The beam must be shaped such that no radiation reaches the critical organ 24 yet the whole target 23 should be treated. To be able to reach the whole target 23 without harming the critical organ 24, a first through field 27 and a second field 29 must be patched together as shown in FIG. 2. The first through field 27 is illustrated in FIG. 2 by two dotted vertical lines and the second field 29 is illustrated by two dashed horizontal lines. In this case second field 29 is shaped in such a way that its distal edge will coincide with a lateral edge of the first field 27 to form an L shape, but even more complex shapes may be necessary in some cases. Because of the difference in dose gradient, it is common that the dose distribution in the border area between the first and the second field is not uniform. Instead the border will normally contain hot and cold spots, which will affect the treatment negatively.

Figure 3:
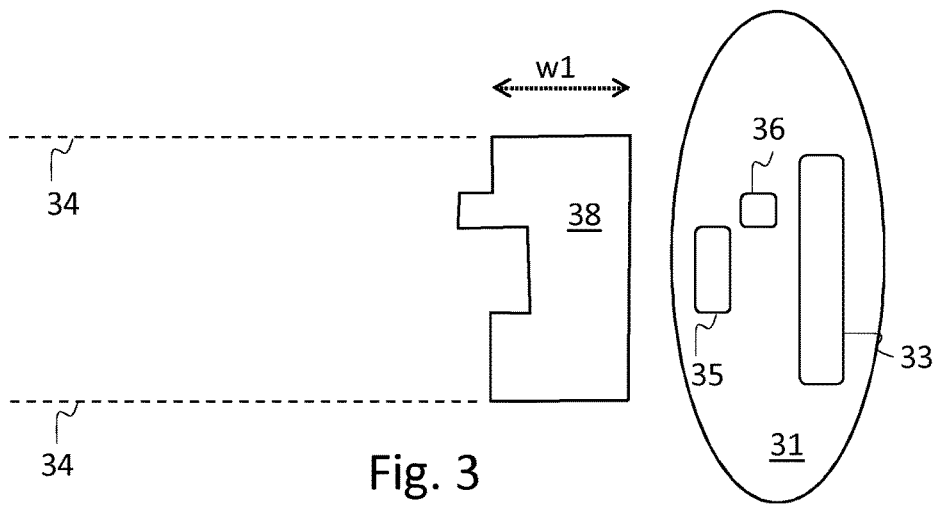
FIG. 3 illustrates another application of the inventive idea for increasing the robustness of a setup.

The method according to the invention also enables uncertainties of the setup to be taken into account in different ways. FIG. 3 illustrates a setup in which this can be applied. A patient 31 has a target ROI 33 which is to receive a target dose of ion radiation represented by two horizontal dashed lines 34. Although the geometrical distance through the patient's body to the distal end of the target is substantially the same across the target, two structures affect the water equivalent distance to the tumour: a bone structure 35 which will add to the water equivalent distance and an air cavity 36 which will reduce the water equivalent distance. As is common in the art, a range compensator 38 is arranged to control the range of the ion beam to match the water equivalent depth. In the areas where the beam will only pass through soft tissue, the range compensator has a first thickness w1. To compensate for the variations in water equivalent depth caused by the bone structure 35 and the air cavity 36, the range compensator 38 has an area in which it is thinner than the first thickness w1, matching the area of the bone structure 35, to compensate for the increased water equivalent distance in this area. The range compensator 38 also has an area in which it is thicker than w1, matching the area of the air cavity 36, to compensate for the reduced water equivalent distance in this area.

As will be seen, if the apparatus, or the patient, is shifted a little bit in one direction, there is a risk that the area of the range compensator that has a higher thickness will affect the beam in an area where the thickness should ideally be the first thickness w1, or where it should be greater than w1, to accommodate the effects of the bone structure 35. Traditionally, such uncertainties are handled by means of smearing techniques, which involves expanding the regions of smaller thicknesses. According to an aspect of the invention such a situation could instead be handled according to the inventive method, by applying a robust optimization method. This includes scenario based inverse planning, where each uncertainty in position and density is discretised and included in the dose computations. The evaluation of the objective function will then look at the combination of all scenarios (or possibly the worst case), instead of just the nominal scenario.

Figure 4:
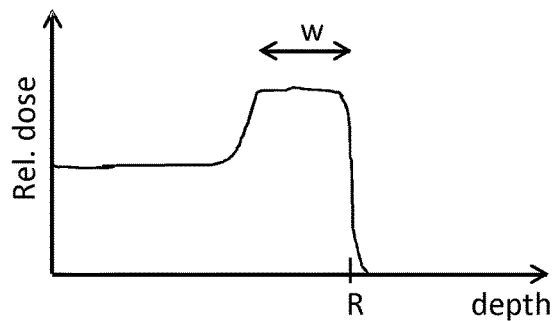
FIG. 4 illustrates the penetration of the proton beam into the patient's body and the spread out Bragg peak (SOBP).

FIG. 4 illustrates schematically the spread out Bragg peak SOBP of a proton beam within a patient in terms of the relative dose as a function of depth. As can be seen, the dose increases from a plateau region to a maximum, which is constant over a distance w. After the spread out Bragg peak the dose will fall to zero within a short distance. The maximum range of the beam is denoted as R. Ideally, the area of the maximum dose should coincide with the target width as shown in FIG. 1, that is, the maximum emitted energy should occur when the proton beam travels through the target, after which the emitted energy should fall to zero as soon as possible. The depth dose shape for other ions is similar to the proton case, except that there will be a low dose tail after the SOBP resulting from nuclear fragments.

To optimize the radiotherapy the range of the beam and the design of the passive devices, that is, the range modulator 9, the block 11 and the range compensator 15, may be varied. Traditionally this is done by forward planning methods, by computing the design of the passive devices through ray tracing of the patient geometry.

For determining the SOBP range, traditionally the maximum range R of the target along the direction of the beam is computed by tracing the water equivalent depths of the distal target edge for all points, i, within the beam. The maximum target range is then computed as the largest water equivalent distance to the distal edge, i.e.

$$\text{maximum target range} = \max_{\forall i} (\text{distal edge}_i) \quad (1)$$

The beam energy is then chosen so that the maximum range of the beam is equal to, or slightly larger than, the maximum range R of the target.

For determining the SOBP width, traditionally the maximum width w of the target along the direction of the beam is computed by tracing the water equivalent depths of the distal and proximal target edges for all points, i, within the beam. The maximum target width is then computed as the largest difference between the distal and proximal edge, i.e.

$$\text{maximum target width} = \max_{\forall i} (\text{distal edge}_i - \text{proximal edge}_i) \quad (2)$$

The range modulator is then chosen so that its corresponding SOBP width is equal to, or slightly larger than, the maximum target width.

For determining the block contour, traditionally all parts of the beam are traced, registering if the target is hit or not, thus finding where the target edge is situated. Due to beam spread the dose will drop at the beam edge, resulting in lower dose at the target edge. This is accounted for by expanding the block contour laterally, typically by 0.5-1 cm. A block contour may range from a few cm up to 20-30 cm across, depending on the size of the target area.

For determining the range compensator traditionally the water equivalent depths of the distal edge for all points, i, within the beam are computed and the corresponding compensator thickness is computed as $$\text{compensator thickness}_i = \text{maximum beam range} - \text{distal edge}_i \quad (3)$$

According to the invention, instead of the methods described above, an inverse planning algorithm is used for determining the final shape of the passive devices using dose based optimization. For this purpose, different optimization variables are defined for the SOBP range and each of the passive devices, that is, the range modulator, the block and the range compensator. The optimization problem is specified by setting up a number of dose optimization functions. With the method according to the invention all devices can be optimized simultaneously.

Figure 5:
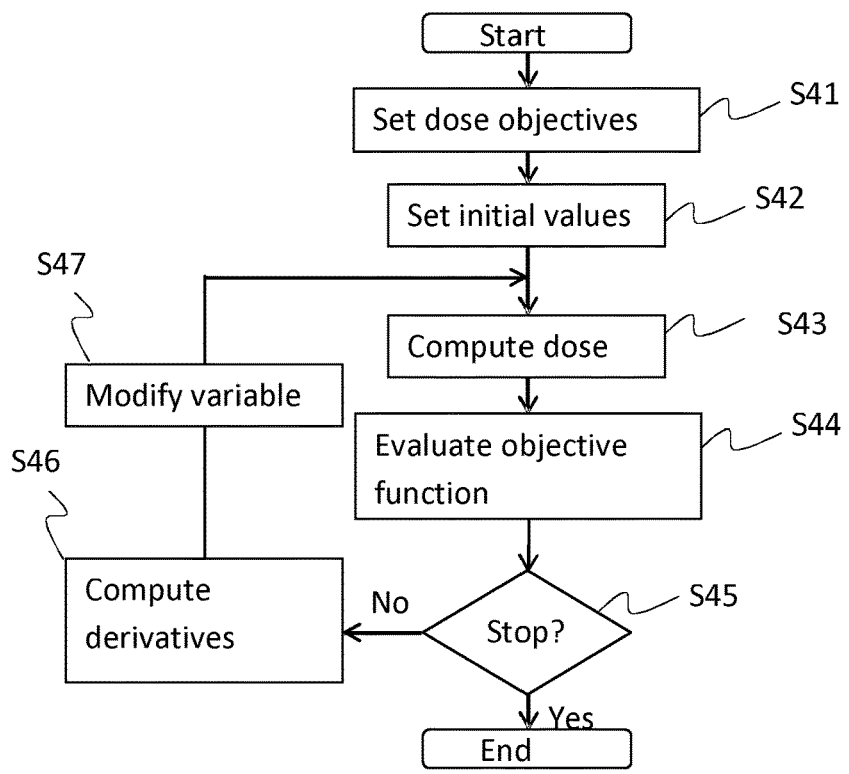
FIG. 5 is a flow chart of a method according to the invention.

As outlined in FIG. 5, the method includes in a first step S41 setting the dose optimization functions and giving them weights, usually including a minimum and maximum dose in the target and a maximum dose in one or more critical risk organs. The combination of the weighted dose optimization functions results in the objective function, which is used to evaluate the dose distribution.

In step S42 an initial set of values for the optimization variables are set and in step S43 the initial resulting dose distribution for this initial set of values is determined. The possible optimization variables for the different devices will be discussed below.

In step S44 the objective function is evaluated by comparing the current dose distribution to the dose objectives, and in step S45 it is determined if the optimization should continue. If yes, the method continues with step S46, otherwise the method ends. Preferably, the optimization continues until the dose distribution satisfies the dose objectives within a certain tolerance. This typically means that the resulting dose to the whole target will be above the minimum dose and the resulting dose to any organ at risk will be below the maximum dose for this organ.

In the optional step S46, the derivative of the objective function with respect to the optimization variables are computed. This can be used to determine the best modification of the optimization variables, described in the next step, although the modification may also be determined in other ways. Details of the derivative computation will be discussed below.

In step S47 at least one of the variable values is varied to produce a modified value set. The resulting dose distribution is computed for the modified set of variable values and the objective function is evaluated with respect to this new dose, i.e. a repetition of step S43 and S44. As mentioned above, normally steps S43-S47 are repeated a number of times, until it is determined in step S45 that the current resulting dose distribution matches the dose objective within a specified tolerance. In that case the last current value set is selected for use in the radiotherapy treatment. Alternatively, the optimization may be continued until the dose distribution substantially does not improve for each iteration, or until a number of iterations have been performed. Alternatively, steps S43-S47 may be repeated a preselected number of times and, among the value sets that have been evaluated, the value set resulting in a dose distribution that best matches the dose objective may be selected.

For the SOBP range and the range modulator, the optimization variables include the range and width of the SOBP. The SOBP range and width should be treated as continuous. In practice this means that they should be changed by very small increments in step S47. Depending on the type of range modulator available for the particular machine, the width may have to be truncated to the next larger range modulator width when finalizing the optimization.

For example, if using an optimization algorithm which is using derivatives, the derivative of dose with respect to the SOBP range or width is computed as a finite difference, i.e. as the difference in dose between a small shift in the range or width ($\Delta w$):

$$\delta[d](t) = d\left(w + \frac{1}{2}\Delta w\right) - d\left(w - \frac{1}{2}\Delta w\right) \quad (4)$$

Although an optimization method using derivatives has been described above, other optimization methods may be used instead, for example an optimization method based on simulated annealing.

For the block 11, two alternative methods are proposed according to the invention:

In the first alternative method the optimization variables for block aperture 13 optimization are expressed as an opening ratio matrix, where each pixel has a value between 0 (completely covered) and 1 (completely open). A pixel value between 0 and 1 means that the pixel is partly covered by the block contour. This leads to the requirement that partly covered pixels must lie on the edge of the open part, with completely covered pixels on the outside. If using an optimization algorithm which is using derivatives, the derivative of dose with respect to opening ratio is equal to the dose contribution from that pixel, since an increase in the opening ratio will result in a proportionally equal increase of dose.

In the second alternative method the optimization variables for block aperture optimization are the positions of all vertices in the block contour polygon. Each vertex may move in the x and y direction. If using an optimization algorithm which is using derivatives, the derivative of dose with respect to the. vertex position may be computed using finite elements, i.e. as the difference in dose between a small shift in the x and y position of the vertex.

For the range compensator 15 the optimization variables are the compensator thickness values in all pixels of the compensator matrix. Preferably, according to the invention each pixel of the compensator matrix may be set individually to allow maximum flexibility of the optimization algorithm.

If using an optimization algorithm which is based on the computation of derivatives, the derivative of dose with respect to the compensator thickness is computed as a finite difference, that is, as the difference in dose between a small shift in thickness (h):

$$\delta[d](t) = d\left(t + \frac{1}{2}h\right) - d\left(t - \frac{1}{2}h\right) \quad (4)$$

The derivative needs to be computed for each compensator pixel in each iteration. In order to speed up the computation, preferably a corresponding dose distribution for a number of compensator thicknesses in each pixel should be precomputed and cached so that the computation does not have to be performed for each dose planning procedure. After that, the derivative computation will be a matter of adding and subtracting cached dose distributions. A suitable range of compensator thicknesses may be +/−1 cm in steps of 1 mm.

The dose derivatives can be used to determine the best modification of the variables in step S47, however they are not necessary for all optimization algorithms.

Figure 6:
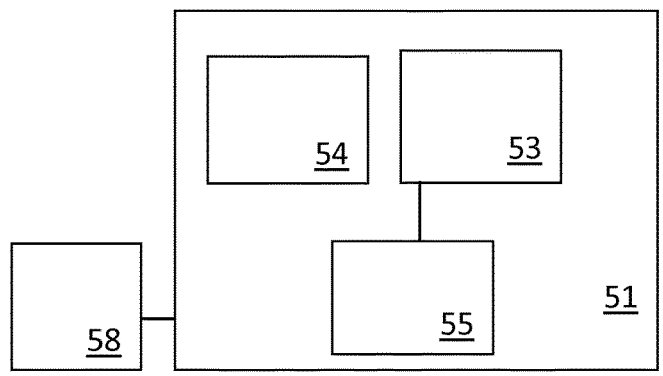
FIG. 6 is a schematic illustration of a computer according to the invention.

To account for the uncertainties of range and setup, the passive devices 9, 11, 15 can be optimized using robust optimization. This means that their shapes are optimized so that the dose is optimal for a number of scenarios that spans the space of all plausible range and setup errors, not just the nominal scenario. Robust optimization, as discussed above, takes into account uncertainties regarding for example the exact position of the patient, or the actual range of the beam FIG. 6 is a schematic representation of a computer system in which the inventive method may be performed. A computer 51 comprises a processor 53, a data memory 54 and a program memory 55. Preferably, a user input means 58 is also present, in the form of a keyboard, a mouse, a joystick, voice recognition means or any other available user input means.

A treatment plan, one or more value sets and one or more objective functions are found in the data memory 54, as well as the tolerance level used in step S45 above. The data in the data memory may be generated in the computer 51, entered by means of the user input means or received from another storage means, in any way known in the art.

As will be understood, the data memory 54 is only shown schematically. There may be several data memory units, each holding one or more different types of data, for example, one data memory for the value set, one for the objective function, etc.

The program memory 55 holds a computer program arranged to control the processor to perform the optimization as defined in FIG. 5. It will be understood that not all of the steps of the method of FIG. 5 are necessarily performed in the computer 51.

The invention claimed is:

1. A method of optimizing a radiotherapy plan for ion therapy, the method comprising the following steps:
   a. defining an objective function comprising at least one dose objective related to a dose to be delivered to a region of a patient by an ion beam shaped by means of passive devices including a range modulator or a ridge filter for adapting the ion beam energy for changing the maximum range of the beam;
   b. defining an initial value set comprising at least one initial value for at least one optimization variable related to the range modulator or the ridge filter, including a value related to a Spread Out Bragg Peak (SOBP) range and width based on the range modulator or ridge filter, and defining the initial value set as a current value set;
   c. determining a dose distribution resulting from the current value set;
   d. evaluating the dose distribution with respect to the dose objectives;
   e. determining if the objective function should be evaluated for another value set and if so, performing step f, otherwise jumping to step g;
   f. modifying at least one initial value in the initial value set to create a modified value set, and defining the modified value set as the current value set before returning to step c;
   g. selecting one of the value sets to be used in the radiotherapy; and h. implementing the radiotherapy for the patient using the ion beam.

2. The method according to claim 1, wherein the determining in step e) is based on whether or not the dose distribution satisfies the dose objectives within a certain tolerance.

3. The method according to claim 1, wherein the dose objective includes a minimum dose for a selected region of the patient and/or a maximum dose for a second selected region of the patient.

4. The method according to claim 1, wherein the passive devices further comprise a range compensator.

5. The method according to claim 1, wherein the passive devices further comprise a block and the at least one optimization variable includes the size and/or shape of an aperture of the block.

6. The method according to claim 5, wherein the block aperture is defined in terms of pixels, or in terms of vertices in a block contour polygon.

7. The method according to claim 4, wherein the initial value set includes a first and a second thickness value in at least a first and a second portion of the range compensator, respectively.

8. The method according to claim 4, wherein the initial value set comprises at least one initial value for each of at least two optimization variables related to at least two of the passive devices.

9. The method according to claim 1, wherein a maximum deviation from the dose objective is set and in step e) it is determined to continue with step g) when a dose distribution that differs from the dose objective by less than the maximum deviation is reached by a modified value set.

10. The method according to claim 1, wherein, in step e) it is determined to continue with step g) when a specified number of value sets have been evaluated, wherein the value set that provides best match with the dose objective is selected.

11. A non-transitory machine-readable medium with machine-readable instructions stored thereon which, when run in a computer, will cause the computer to perform the method according to claim 1.

12. A computer system for performing dose calculations for radiotherapy, the system comprising:
at least one non-transitory program memory storing instructions; and
one or more hardware processors that are coupled to the at least one non-transitory program memory and that are configured to execute the instructions to cause the computer system to perform the method according to claim 1.

13. The computer system according to claim 12, further comprising a data memory arranged to hold data to be used by the one or more hardware processors when performing the optimization method, the data comprising image data related to the patient, an initial treatment plan, or information related to at least one scenario.

* * * * *